US008133457B2

(12) United States Patent
Ribault et al.

(10) Patent No.: US 8,133,457 B2
(45) Date of Patent: Mar. 13, 2012

(54) UNIT FOR PREPARING A SAMPLE FOR THE MICROBIOLOGICAL ANALYSIS OF A LIQUID

(75) Inventors: Sebastien Ribault, Romanswiller (FR); Gael Waiche, Molsheim (FR); Emmanuelle Simon, Schnersheim (FR); Luc Felden, Colmar (FR)

(73) Assignee: Millipore Corporation, Billerica, MA (US)

( * ) Notice: Subject to any disclaimer, the term of this patent is extended or adjusted under 35 U.S.C. 154(b) by 90 days.

(21) Appl. No.: 12/459,879

(22) Filed: Jul. 9, 2009

(65) Prior Publication Data

US 2010/0012589 A1    Jan. 21, 2010

(30) Foreign Application Priority Data

Jul. 16, 2008   (FR) ...................................... 08 54844

(51) Int. Cl.
*B01D 61/14* (2006.01)
(52) U.S. Cl. ..... 422/513; 422/535; 422/559; 210/321.6; 210/323.1
(58) Field of Classification Search .................. 422/513, 422/535, 559; 210/321.6, 322, 323.1
See application file for complete search history.

(56) References Cited

U.S. PATENT DOCUMENTS

| | | | |
|---|---|---|---|
| 2,923,669 A | 2/1960 | Poitras | |
| 3,211,645 A * | 10/1965 | Ferrari | ......................... 210/637 |
| 4,215,198 A | 7/1980 | Gordon | |
| 4,317,726 A | 3/1982 | Shepel | |
| 4,450,078 A * | 5/1984 | Walker et al. | ................. 210/315 |
| 4,528,933 A * | 7/1985 | Allen | ............................ 116/308 |
| 5,116,754 A | 5/1992 | Fraser et al. | |
| 5,139,031 A | 8/1992 | Guirguis | |
| 5,208,161 A | 5/1993 | Saunders et al. | |
| 5,342,581 A * | 8/1994 | Sanadi | .......................... 422/552 |
| 6,300,142 B1 | 10/2001 | Andrewes et al. | ............ 436/518 |
| 6,374,684 B1 | 4/2002 | Dority | ........................ 73/864.81 |
| 2003/0085228 A1* | 5/2003 | Oakes | .......................... 220/302 |
| 2004/0009473 A1 | 1/2004 | Pease | |
| 2004/0185437 A1 | 9/2004 | Hermet et al. | |
| 2004/0219628 A1 | 11/2004 | Tashiro et al. | |

(Continued)

FOREIGN PATENT DOCUMENTS

GB        2 297 926 A1    8/1996

OTHER PUBLICATIONS

Office Actions dated Feb. 26, 2009, May 26, 2009, Jul. 30, 2009, Dec. 29, 2009 and Apr. 20, 2010 in co-pending U.S. Appl. No. 11/805,539.

(Continued)

*Primary Examiner* — In Suk Bullock
*Assistant Examiner* — Paul Hyun
(74) *Attorney, Agent, or Firm* — Nields, Lemack & Frame, LLC

(57) ABSTRACT

The unit comprises a filter membrane filter module and a collection module for liquid coming from the filter module, with the filter module comprising an inlet compartment as well as an evacuation compartment for the liquids, the filter and collection modules being rotatably mounted relative to each other. The method comprises the step of obtaining such a unit, of disposing the filter and collection modules in a first position, of passing a liquid from the filter module to attain the collection module, of disposing the filter and collection modules relative to each other in a second position, and the step of passing another liquid from the filter module to attain the collection module.

22 Claims, 10 Drawing Sheets

U.S. PATENT DOCUMENTS

| | | | | |
|---|---|---|---|---|
| 2004/0248774 | A1* | 12/2004 | Tayot | 514/2 |
| 2006/0257993 | A1 | 11/2006 | McDevitt et al. | |
| 2007/0298451 | A1 | 12/2007 | Ribault et al. | |
| 2009/0181450 | A1 | 7/2009 | Ribault et al. | |
| 2011/0174735 | A1 | 7/2011 | Ribault et al. | |

OTHER PUBLICATIONS

Final Rejection dated Jan. 7, 2011 in co-pending U.S. Appl. No. 11/805,539.
Office Action dated Aug. 27, 2010 in co-pending U.S. Appl. No. 11/805,539.
Office Action dated Apr. 21, 2011 in co-pending U.S. Appl. No. 11/805,539.
Final Rejection mailed Oct. 18, 2011 in co-pending U.S. Appl. No. 11/805,539.
Advisory Action mailed Nov. 25, 2011 in co-pending U.S. Appl. No. 11/805,539.
Office Action mailed Nov. 1, 2011 in co-pending U.S. Appl. No. 12/383,131.

* cited by examiner

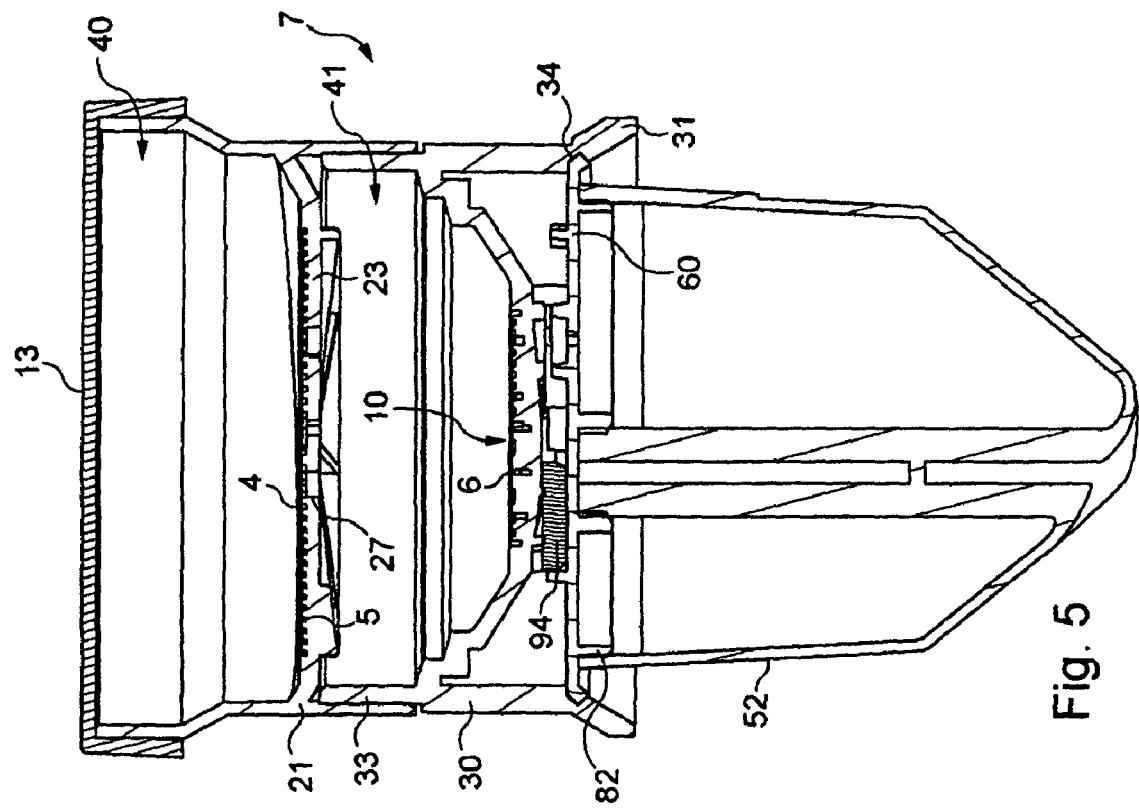
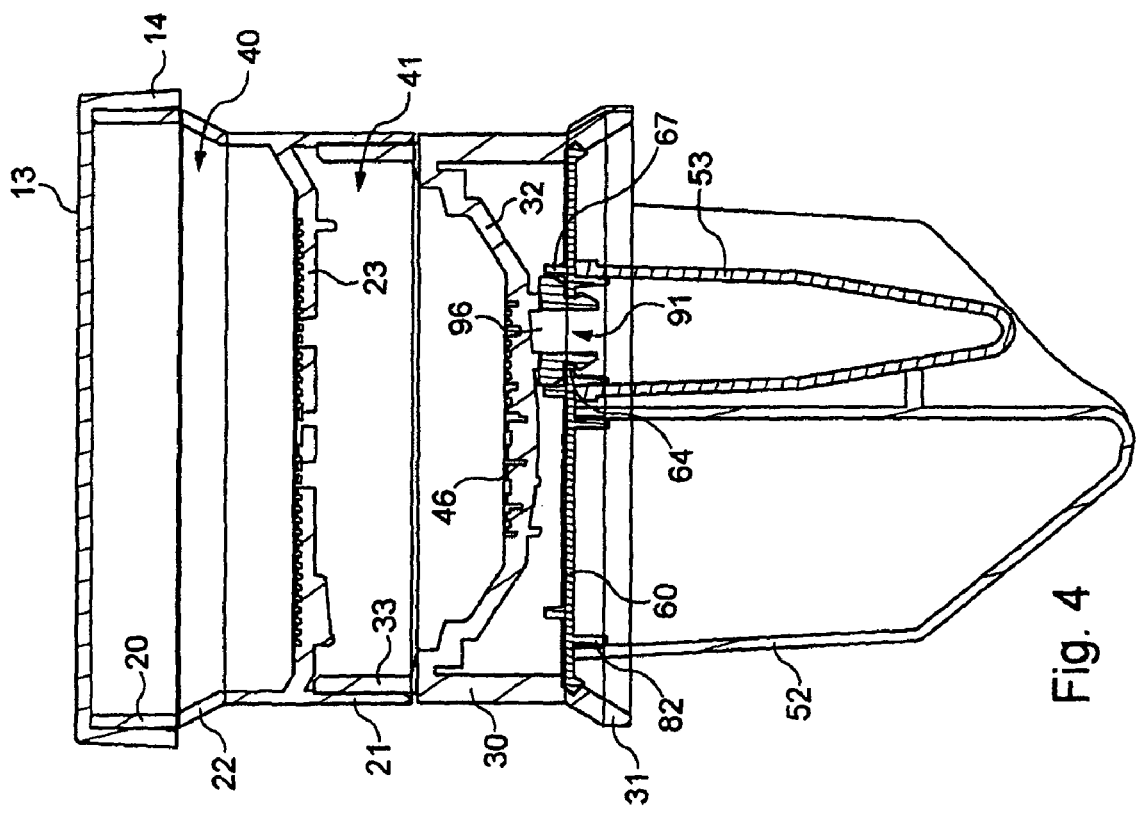
Fig. 5
Fig. 4

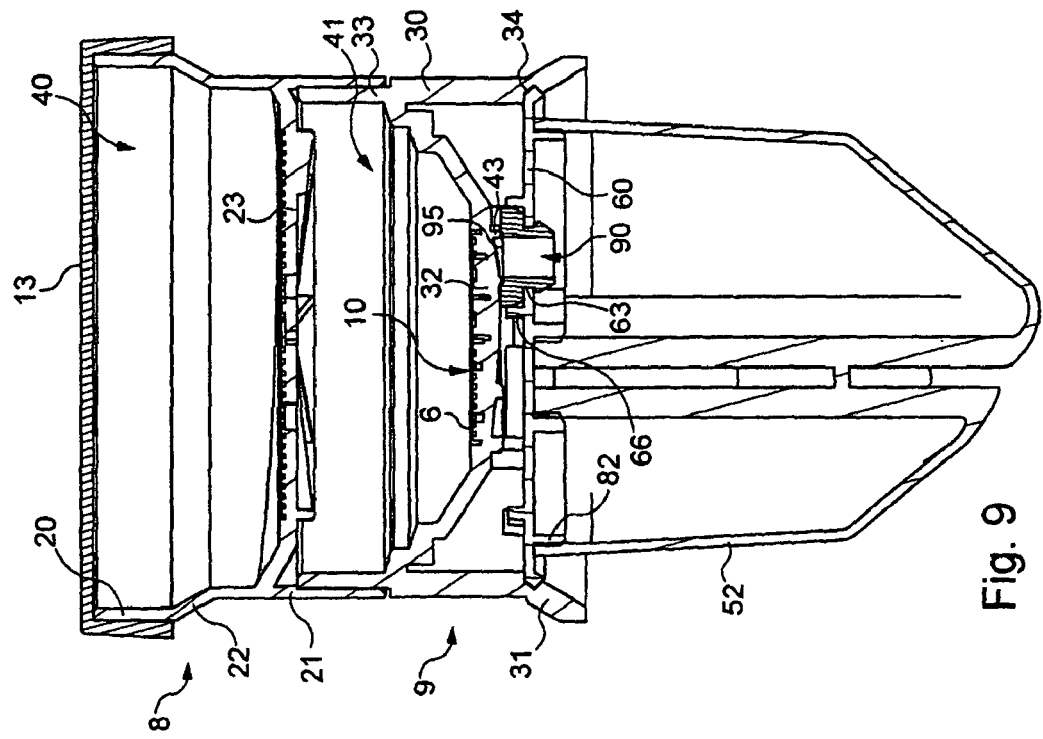
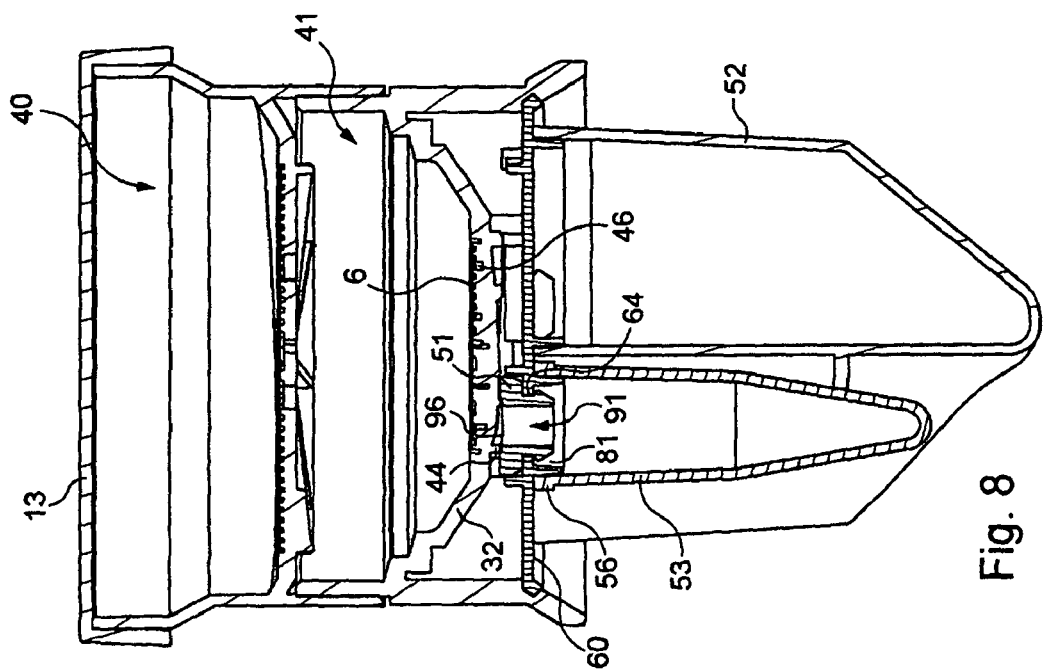

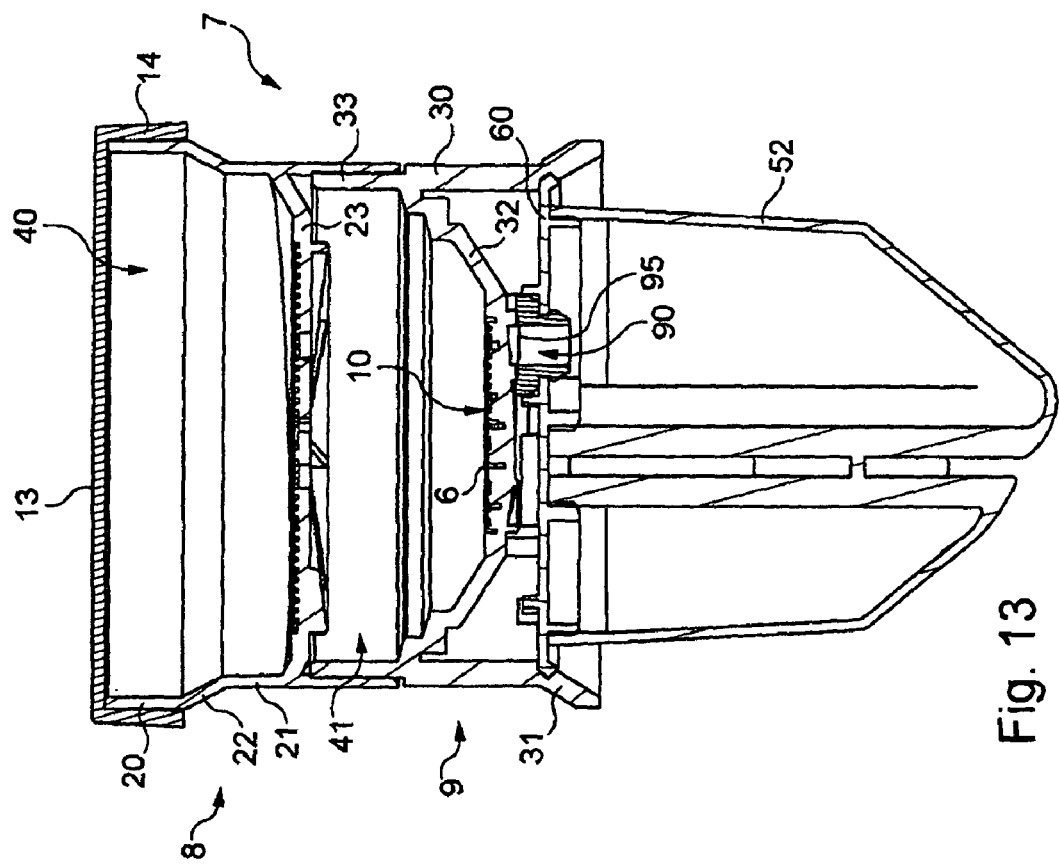
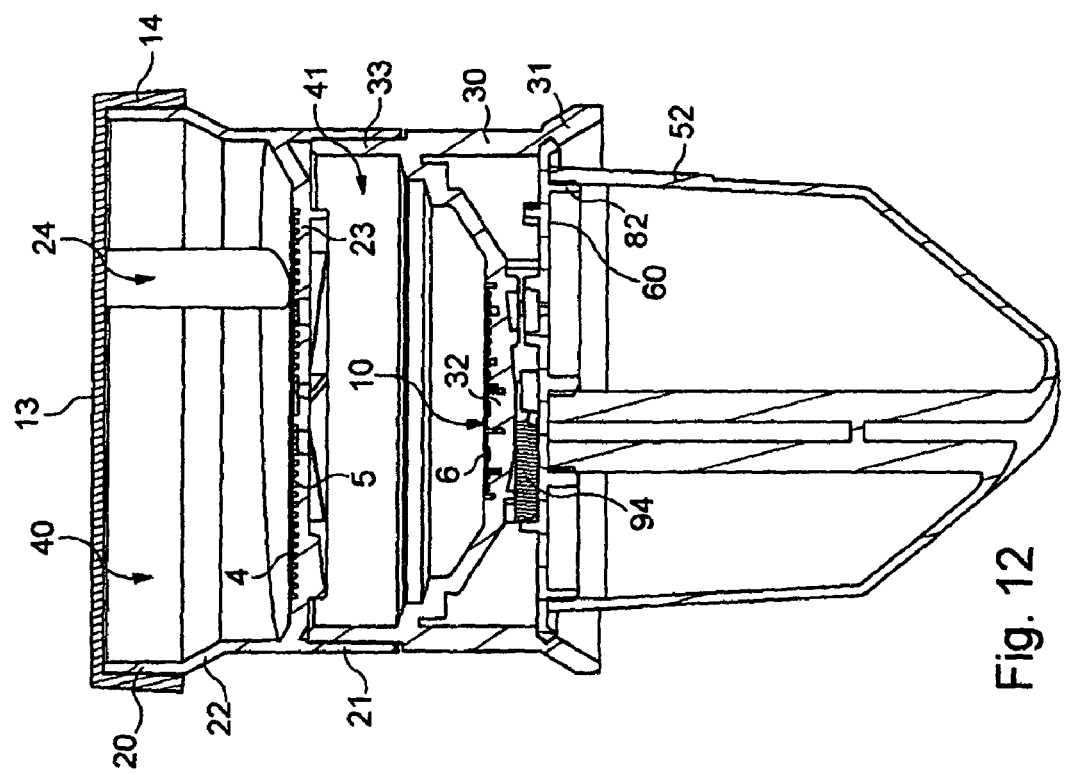
Fig. 12
Fig. 13

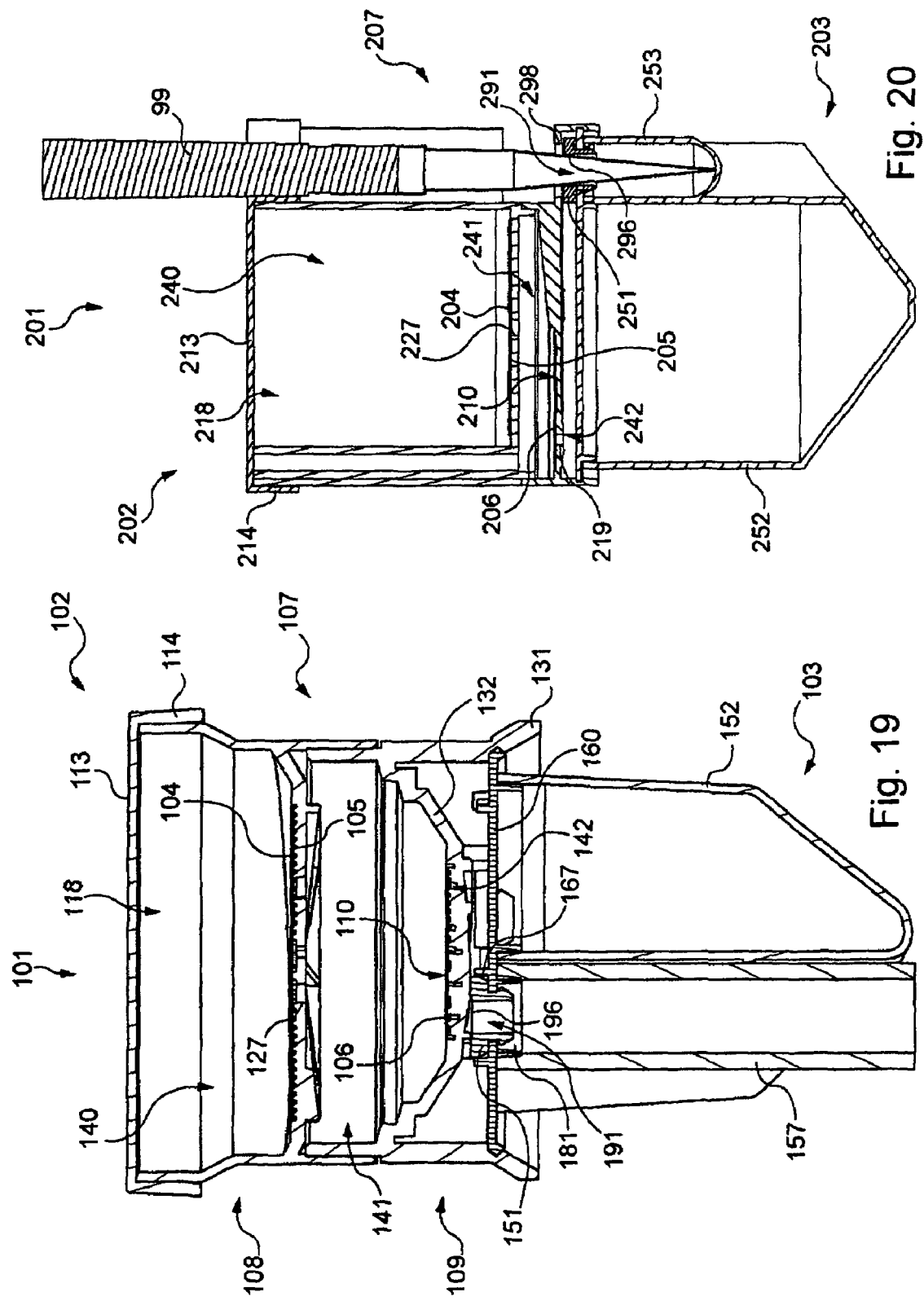

UNIT FOR PREPARING A SAMPLE FOR THE MICROBIOLOGICAL ANALYSIS OF A LIQUID

The present invention concerns the preparation of a sample for the microbiological analysis of a liquid.

The preparation of such samples is most commonly carried out by passing a liquid that may contain microorganisms through a preparation unit provided with a filter membrane on which the microorganisms of that liquid are retained if it contains any.

Such preparation units are provided for inletting a predetermined volume of liquid to analyze into a compartment of that unit, in order to pass that liquid through the membrane and to evacuate the liquid once it has crossed the membrane.

In some cases is its sometimes necessary also to collect the liquid that has crossed the membrane after having undergone a treatment specific to the microorganisms that it may retain (such as a treatment by lysis of those microorganisms for the purpose of collecting the biological material of those microorganisms for analyses) but without that liquid mixing with the liquid filtered previously.

A preparation unit is already known from the U.S. Pat. No. 6,374,684 comprising a compartment for inletting a liquid to analyze, a plurality of compartments disposed around the inlet compartment, as well as a rotary valve overhanging those compartments and adapted to make those compartments communicate pairwise, either directly, or via a filter membrane that the valve comprises.

A plunger slides in the inlet compartment not only to be able to take off liquid by sucking (by pulling the plunger) from one of the of the compartments surrounding the inlet compartment, but also, after rotation of the valve, to be able to collect that liquid (by pushing the plunger) in another of the compartments surrounding the inlet compartment, either directly, or after that liquid has crossed the filter membrane.

The invention concerns providing a unit of the same type but which at the same time is more polyvalent and more practical.

To that end it provides a unit for preparing a sample for the microbiological analysis of a predetermined volume of liquid that may contain microorganisms comprising a filter membrane filter module and a collection module for each liquid coming from said filter module, with said filter module comprising an inlet compartment for inletting said predetermined volume by an inlet opening of said filter module, said inlet compartment being adapted to contain the whole of said predetermined volume, as well as an evacuation compartment for evacuating said predetermined volume by an evacuation opening of said filter module to said collection module, said evacuation compartment being separated from said inlet compartment by said membrane, the filter and collection modules being rotatably mounted relative to each other, and having, relative to each other, a first relative predetermined position, in which said evacuation opening of said filter module is in register with a first opening of said collection module and a second relative predetermined position different from said first position, in which said evacuation outlet of said filter module is in register with a second opening of said collection module; characterized in that said inlet and evacuation compartments are on opposite sides from each other relative to said filter membrane with said inlet compartment being arranged such that, when said predetermined volume is in said inlet compartment, the liquid is in contact with the filter membrane over at least the majority of its surface.

The arrangement of the inlet and evacuation compartments on the opposite side from each other relative to the filter membrane with the inlet compartment which enables the liquid to be placed in contact with at least the majority of the surface of the membrane gives numerous possibilities for making the liquid flow from the filter module to attain the collection module.

The flow of the liquid into the preparation unit across the membrane may thus be implemented for example by placing that unit in a centrifuge.

More particularly, the fact that the inlet compartment for the liquid and the evacuation compartment are on opposite sides from each other relative to the membrane (that is to say on either side of the membrane) thus enables the liquid to flow in a single direction for the entire length of the filtration, so making the unit compatible with the liquid flowing by centrifuging.

Furthermore, when situated at the level of the inlet compartment, the liquid comes into contact with the membrane over the majority of its surface so giving a large area for liquid passage, the pressure loss thus being rendered small also to enable flow by centrifuging.

This is an advantage relative to the devices of the prior art, such as those described in particular in the U.S. Pat. No. 6,374,684, which did not provide such a possibility due to the fact that the compartments of those devices are all situated on the same side of the membrane (centrifuging of such devices thus not making it possible to pass the liquid from one compartment to another) and also due to the fact that the liquid of the inlet compartment is not in direct contact with the membrane over the majority of its surface but via a narrow channel making that arrangement incompatible with the passage of the liquid by centrifuging, the restriction in cross section in the liquid flow zone being too great.

According to features preferred for reasons of simplicity and convenience with regard both to manufacture and to use, in said first predetermined position, said second opening is obturated and, in said second predetermined position, said first opening is obturated.

According to other preferred features, said filter and collection modules also have another predetermined position relative to each other, termed obturating position, different from the first and second positions, in which said evacuation opening is obturated.

In this position in which the evacuation opening is obturated, it is possible to deposit a reagent in the filter module without it flowing through the collection module. It may thus be a chemical lysing agent to perform lysis of the microorganisms retained on the filter membrane. As this agent is unable to flow out, its action is more effective on the microorganisms due to a longer contact time. It is thus possible to use a small volume of that agent which improves the sensitivity of the analyses carried out on the lysate so obtained (as too great a volume of reagent can be a source of background noise in particular for analyses such as methods of nucleic acid amplification.

According to other preferred features:
in said obturating position, said first and second openings are also obturated; and/or
said filter and collection modules also have another predetermined position relative to each other, termed take-off position, different from the first and second positions, in which said second opening is in register with a take-off opening that said unit comprises.

According to still other preferred features, said filter module comprises a body within which is fixed said filter membrane as well as a separation membrane that is situated between said inlet opening and said filter membrane, said separation membrane having a pore diameter greater than the pore diameter of said filter membrane.

The presence of two membranes in the filter module of different pore diameters makes it possible to separate the unwanted microorganisms (for example eukaryote cells, which are of too large a size to pass through the membrane) from the microorganisms to analyze (bacteria or viruses for example) which are collected on the second membrane.

According to other preferred features, said separation membrane is fixed to a first portion of said body and said filter membrane is fixed to a second portion of said body, with said first and second portions being adapted to be nested one inside the other and welded together.

According to other preferred features, said filter module comprises another membrane, juxtaposed against said separation membrane, on the opposite side of the separation membrane to the filter membrane, said other membrane having a greater pore diameter than the pore diameter of said separation membrane.

The presence of another membrane juxtaposed against the separation membrane and of greater pore diameter prevents the clogging phenomena which could occur on the separation membrane if it were alone, in particular where the liquid to filter is particularly laden with cells to separate from the microorganisms to analyze.

According to other preferred features:
the pore diameter of said separation membrane is greater than 1 µm; and/or
the pore diameter of said filter membrane is less than 1 µm.

According to other preferred features, said filter module comprises another opening formed in said body and giving access to a compartment of said body situated between said separation and filter membranes.

This opening thus makes it possible to easily access the filter membrane to deposit thereon a reagent such as an agent for lysing the microorganisms it retains.

According to other preferred features:
said opening is situated at the end of a channel formed in said body;
said opening of said channel is substantially situated at the same level as the inlet opening of the liquid that may contain microorganisms;
said collection module comprises a disc of which the perimeter is adapted to be received in an annular groove that said filter module comprises;
said filter module comprises indexing means and said collection module comprises complementary indexing means for each predetermined position of the filter module relative to the collection module;
said indexing means comprise a fin and said complementary indexing means comprise ribs each having a cut-out adapted to receive said fin;
said first opening of the collection module issues to a reservoir that said collection module comprises;
the collection module comprises a vent adapted allow air to pass into said reservoir;
said reservoir has a crescent-shaped cross-section;
said second opening of the collection module issues to a reservoir that said collection module comprises;
said reservoir has latching means adapted to cooperate with complementary latching means that said collection module comprises;
said collection module comprises a seal in which are formed two ducts, each respectively issuing, on the same side as the filter module, by said first opening and by said second opening;
said seal has a bean-shaped cross-section; and/or
said filter module comprises a vent adapted to allow air to pass into said inlet compartment.

According to a second aspect the invention also concerns a method of preparing a sample for the microbiological analysis of a predetermined volume of liquid that may contain microorganisms, characterized in that it comprises:
the step of obtaining a preparation unit as set forth above;
the step of disposing the filter module and collection module of that unit relative to each other in said first predetermined position;
the step of passing said predetermined volume of liquid that may contain microorganisms from the filter module to attain the collection module through said evacuation opening of the filter module and through said first opening of the collection module;
the step of disposing the filter module and collection module relative to each other in said second predetermined position; and
the step of passing a predetermined volume of another liquid from the filter module to attain the collection module through said evacuation opening of the filter module and through said second opening of the collection module.

According to features preferred for reasons of simplicity and convenience with regard both to manufacture and to use:
said steps of passing said predetermined volumes from the filter module to attain the collection module are implemented by centrifuging;
said method comprises, prior to said step of passing said predetermined volume of said other liquid through said evacuation opening of the filter module and through said second opening of the collection module, the step of selecting as other liquid, a liquid adapted to cause the lysis of the microorganisms retained on said filter membrane, the step of depositing on said filter membrane said predetermined volume of said other liquid, and then the step of leaving said other liquid to act on said microorganisms for a predetermined time; and/or
said method comprises, subsequent to the step of passing said predetermined volume of said other liquid through said evacuation opening of the filter module and through said second opening of the collection module, the step of retrieving said predetermined volume of said other liquid for analysis.

The features and advantages of the invention will appear from the following description, given by way of preferred but non-limiting example, with reference to the accompanying drawings in which:

FIG. 1 is an exploded perspective view of a preparation unit according to the invention;

FIGS. 2 to 5 are respectively a perspective view and three views in cross-sectional elevation in different section planes of that preparation unit in which there are represented a collection module for the liquids and a filter module for those liquids which that unit comprises, the filter and collection module being disposed relative to each other in a relative angular position enabling the liquid to flow from the filter module to a first reservoir of the collection module by an evacuation aperture of the filter module.

FIGS. 6 to 9 are similar views to FIGS. 2 to 5 but illustrating the preparation unit in another relative angular position in which the evacuation aperture which enabled the flow of the liquid from the filter module to the collection module is obturated;

FIGS. 10 to 13 are similar views to FIGS. 2 to 5 but illustrating the preparation unit in still another relative angular position enabling the liquid to flow from the filter module to a second reservoir of the collection module by the evacuation aperture;

FIGS. 19 and 20 are sectional views in elevation respectively illustrating a second and a third embodiment of the preparation unit according to the invention.

Figure 1:
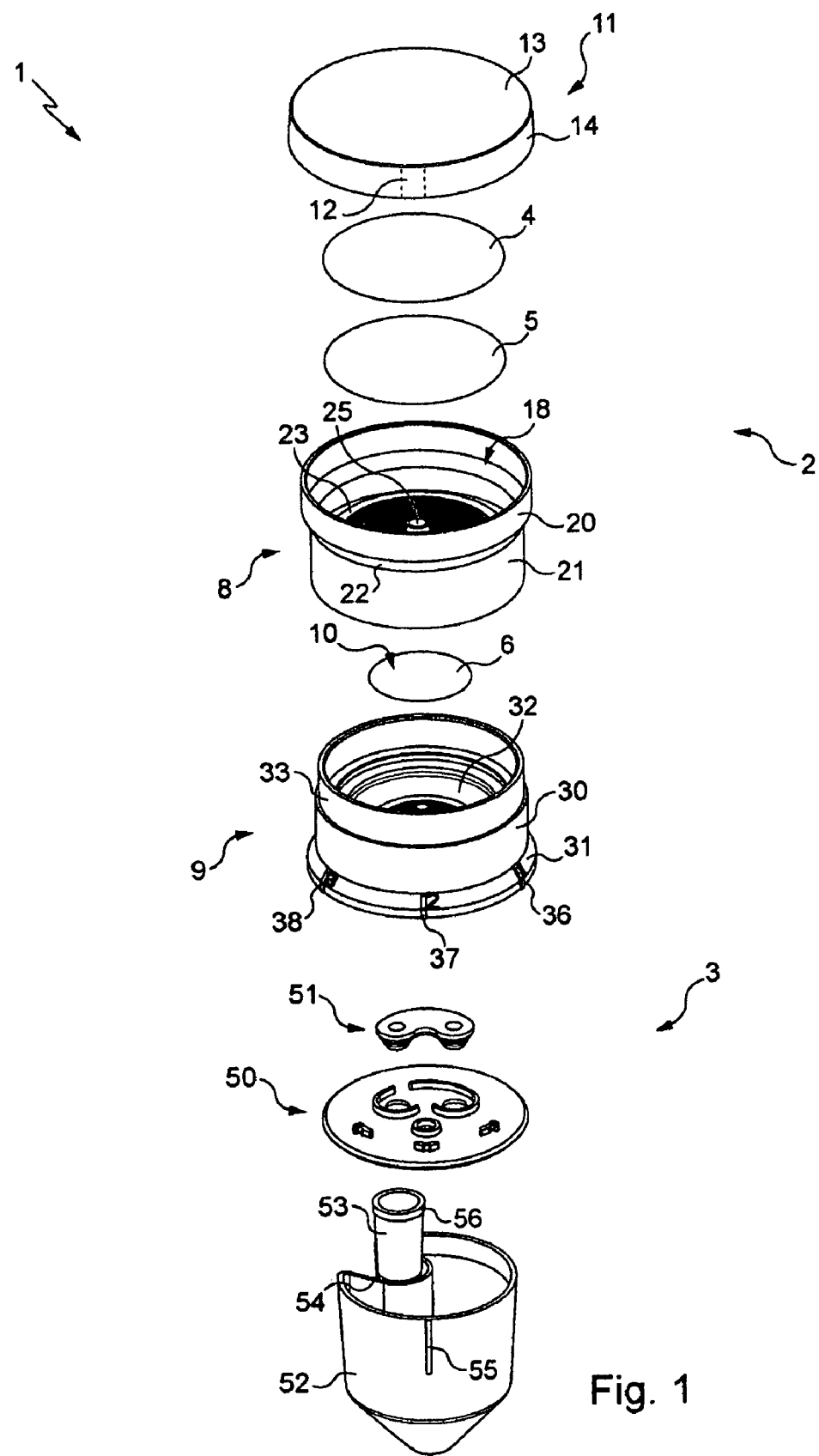

The preparation unit 1 illustrated in FIGS. 1 to 13 comprises a filter module 2 and a module 3 for collection of the liquids after they have passed through the filter module.

The filter module comprises three filter membranes 4, 5 and 6, a body 7 (FIG. 3) as well as a cover 11 nestingly fitted around the body and obturating it.

This cover 11 has a wall 13 and an annular collar 14 with, in the collar 14, a groove 12 which is locally formed on the inner face of that collar (represented in dashed line in FIG. 1) to form, as will be seen below, a vent allowing air to pass.

The body 7 has an upper portion 8 and a lower portion 9 with one nested in the other.

Figure 14:
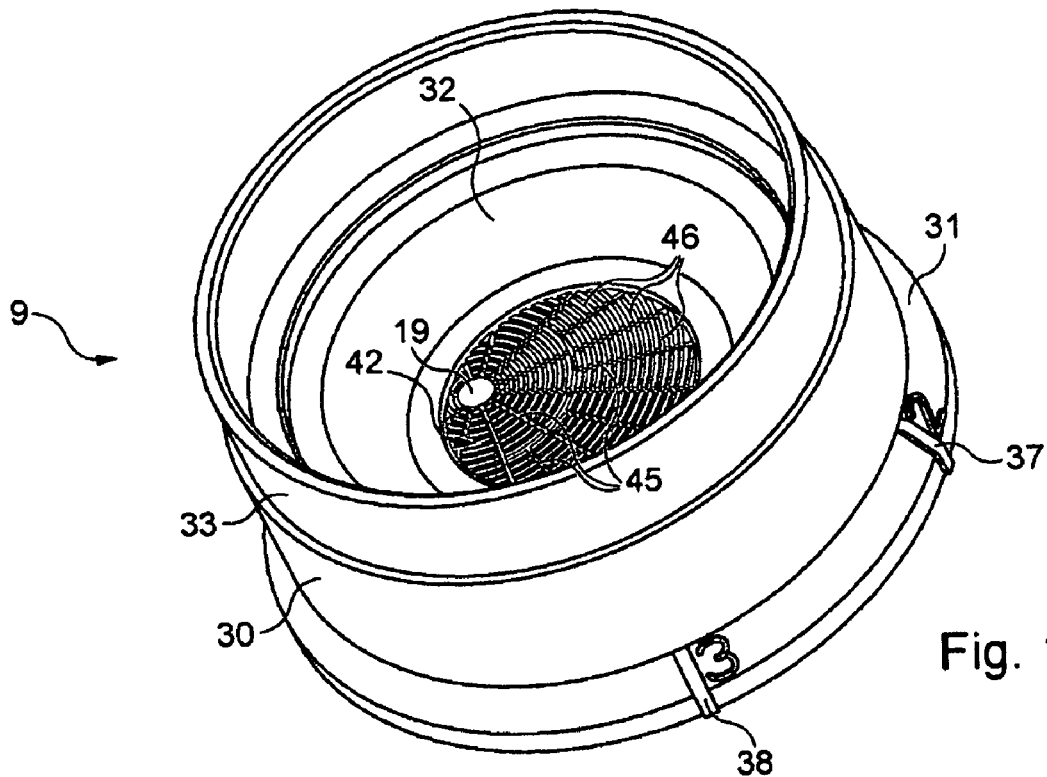
FIGS. 14 and 15 are respectively a perspective view from above and a perspective view from below presenting a portion of the filter module body in isolation.

The portion 8 has an inlet opening 18 for the liquid while portion 9 has an evacuation opening 19 (FIGS. 3, 14 and 15) for that liquid.

Portion 8 has a first cylindrical part 20 delimiting the opening 18 and around which the cover 11 nestingly fits and a second cylindrical part 21 of smaller diameter than the first cylindrical part 20, these parts being connected together by a frusto-conical part 22. The cylindrical part 21 is closed, on the opposite side to the frusto-conical part 22 by a wall 23 with the exception of an opening 27 (FIG. 3) for passage of the liquid to the following compartment. The membranes 4 and 5 (disposed against each other) are sealed against that wall at their perimeter.

The membranes 4 and 5 are formed from polypropylene, the pore diameter of the membrane 4 being equal to 30 μm whereas the pore diameter of the membrane 5 is equal to 5 μm.

These membranes rest on a region of the wall 23 in which are formed drainage channels for the liquid after having passed through those membranes, the channels being provided to direct the liquid to the passage opening 27. The width of the channels (0.4 mm) is chosen so as to provide sufficient drainage of the liquid while ensuring sufficient mechanical support for the membranes 4 and 5 which must resist high pressure stresses in particular in case of filtration by centrifuging.

In portion 8 there is also formed a channel 24 (FIG. 3) open at both ends, disposed against the inner face of part 21 and extending beyond that part towards the opening 18. The opening 25 of that channel is situated substantially at the level of the opening 18, and is obturated by the cover 11 when it is nestingly fitted around part 20, that channel issuing, by its opposite opening 26 to the opening 25, into the region of the filter module situated between the membrane 6, and the membranes 4 and 5.

Portion 9 has a cylindrical part 30, a frusto-conical part 31 and a transverse wall 32.

The cylindrical part 30 is of substantially equal diameter to the diameter of the cylindrical part 21 and has a region 33 of reduced thickness provided to be nestingly fitted by deformation of part; 21 and then welded against that part 21 to provide the integrity of the unit relative to leaks on centrifuging but also relative to risks of contamination (in particular when it is not possible to work under an extractor hood).

The frusto-conical part 31 is connected to the part 30 on the opposite side to that provided to be nestingly fitted into portion 8 and tapers outwardly.

At regular intervals on that part are overprinted the FIGS. "1", "2" and "3" respectively corresponding, as will be seen below, to the three relative angular positions which the filter and collection modules are adapted to take relative to each other. Beside each of these inscriptions is disposed a corresponding rib (36 for the FIG. "1", 37 for the FIG. "2" and 38 for the FIG. "3") for reading the associated position.

An annular groove 34 is formed in part 30 on its inner face and in the neighborhood of the junction with the frusto-conical part 31.

From the inner face of part 30 an indexing fin 35 (FIG. 15) also projects, which is provided for cooperating with complementary indexing means on the collection module 3 to hold the filter module relative to the collection module in the desired position.

The transverse wall 32 extends substantially transversely to the cylindrical part 30 while partially obturating it and joining to the part 30 at approximately half way between its edges. This wall has a step formation at its periphery to form a bowl at the bottom of which is sealed the membrane 6 around its perimeter.

Figure 15:
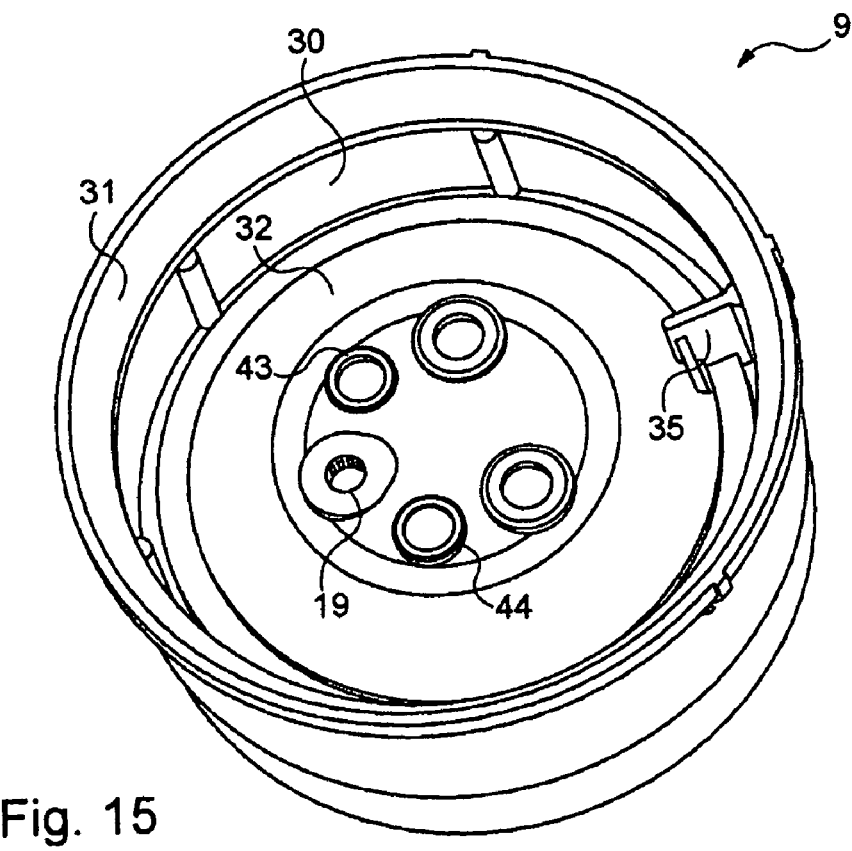
Figure 16:
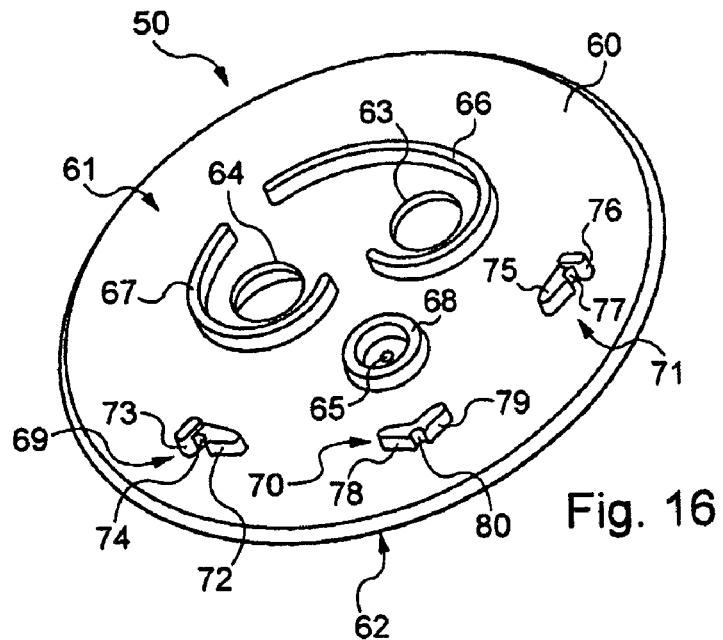
FIGS. 16 and 17 are two views similar to FIGS. 14 and 15 illustrating a disc for distributing the liquids that the collection module comprises and which cooperates with the filter module.
Figure 17:
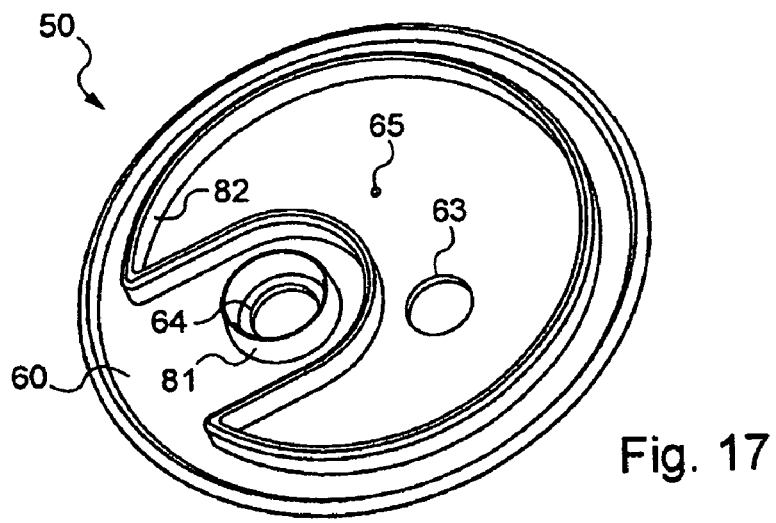

From that wall, on the opposite side to that provided for cooperating with the membrane 6, and as illustrated in FIG. 15, project two annular ribs 43 and 44.

In that wall there is formed a circular opening forming the opening 19 for evacuation of the liquid.

The membrane 6 is formed from polyvinylidene fluoride (PVDF) and has pores of diameter equal to 0.45 μm, it rests on a region of the wall 32 in which are formed drainage channels 46 (FIG. 14) for the liquid passing through the membrane, those channels being provided to direct the liquid to ducts that join to the evacuation opening 45. These ducts are inclined in order to ensure minimum retention of the liquid under the membrane in particular on retrieval of the lysate when centrifuging.

The portion 8 delimits a first compartment 40 together with the membranes 4 and 5, in the nested state the portions 8 and 9 delimit a second compartment 41 together with the membranes 4 and 5 on one side and the membrane 6 on the other side, while the portion 9 delimits, together with the membrane 6, a third compartment 42 (formed in particular by the drainage channels 46 and by the space situated adjacent the ducts 45 and the opening 19).

This filter module is thus arranged such that the introduction compartments for the liquid, formed from the compartments 40 and 41, and the evacuation compartment 42 for the liquid are on opposite sides from each other relative to the membrane 6 (that is to say on either side of the membrane 6) so as to enable the liquid to flow in a single direction for the entire length of the filtration, so making the unit compatible with the liquid flowing by centrifuging.

When the liquid is situated at the level of compartment 41 it comes into contact with the membrane 6 over its surface 10 so giving a large area for liquid passage also to enable its flow by centrifuging.

The collection module 3 comprises a fluid distribution disc 50, a fluid-tight seal 51, as well as a first reservoir 52 and a second reservoir 53 attached on the same side of the disc 50.

The reservoir 52 is sealed by laser welding against the disc 50 and is provided to collect the liquid which has been filtered through the three membranes and which is not intended to be analyzed. The reservoir 52 has a crescent-shaped cross-section (FIG. 1) such that it thus has a recessed region 54 in which the reservoir 53 is accommodated. From the outer surface of the reservoir 52 projects a rib 55, which, as will be seen below, forms a cursor for reading the position of the filter module 2 relative to the collection module 3.

The reservoir 53 has smaller capacity than the reservoir 52, and is a collector tube here of microtube type with 1.5 mL capacity. This reservoir 53 is provided as will be seen below for collecting microorganisms to analyze after having subjected them to lysis on the membrane 6.

The reservoir 53 has a rim 56 provided for latching cooperation with a collar 81 of the disc 50.

This disc 50 has a wall 60 in which there are formed two openings 63 and 64 of the same diameter and an opening 65 of markedly smaller diameter than that of the openings 63 and 64, the openings 63, 64 and 65 respectively being surrounded by ribs 66, 67 and 68 projecting from the face 61 of the wall 60 that is situated on the opposite side to the reservoirs 52 and 53.

The rib 68 surrounding the aperture 65 is circular.

This disc also comprises three ribs 69, 70 and 71 projecting from that surface 61, each provided to form, as will be seen below, a housing for indexing the position of the collection module relative to the filter module.

The rib 69 (respectively 71) has a guide portion 72 (respectively 75) for the indexing fin 35 that the filter module comprises, an abutment portion 73 (respectively 76) for that fin and a housing-forming cut-out 74 (respectively 77) for that fin situated between the portions 72 and 73.

The intermediate rib 70 has two guide portions 78 and 79, and a cut-out 80 between those portions.

This disc also comprises, projecting from the opposite face 62 to the face 61, an annular collar 81 for latching to the reservoir 53 and an annular collar 82 for centering the reservoir 52 welded against that disc.

The seal 51 is a seal of elastomer (of silicone in the example illustrated) of bean-shaped longitudinal section in which, in the neighborhood of each end, there is formed a passage duct 90, 91 for the liquid coming from the filter module. Around the duct 90 (respectively 91) there is formed an annular groove 92 (respectively 93) formed to accommodate therein the portion of the wall 60 of the disc 50 bordering the opening 63 (respectively 64).

Figure 18:
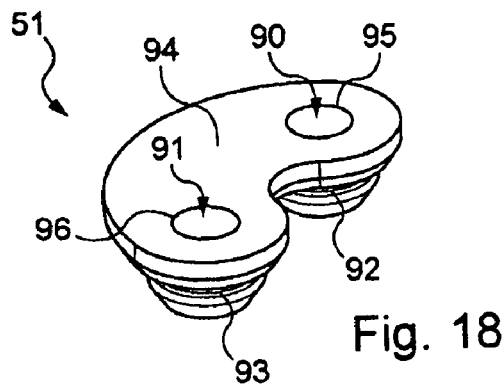
FIG. 18 is a perspective view presenting in isolation a seal that the filter module comprises and which cooperates with the disc for distributing the liquids.

The duct 90 (respectively 91), as illustrated in FIG. 18, issues on the side of the seal provided to cooperate with the filter module 2 by a first opening 95 (respectively 96) and on the opposite side by a second opening (not visible in the drawings).

In the nested position of the seal 51 in the disc 50, the ribs 66 and 67 partially surround that seal.

The wall 60 of the disc 50 is received at its periphery in the annular groove 34 of the filter module, such that the filter module is thus rotatably mounted relative to the collection module, the fin 35 of the filter module being provided to be received in one of the cut-outs 74, 77 or 80 of the collection module depending on the step of preparing the sample that is implemented (see below).

In the latched position of the disc 50 of the collection module 3 in the groove 34 of the filter module 2, the seal 51 is compressed between the wall 60 of the disc and the wall 32 of the filter module, this compression enabling the passage of the liquids from one module to the other without risk of leakage (fluid-tight connection).

The filter module 2 is thus provided to have three distinct positions relative to the collection module 3 with the fin 35 of the filter module being latched in the corresponding housing for each position.

Figure 3:
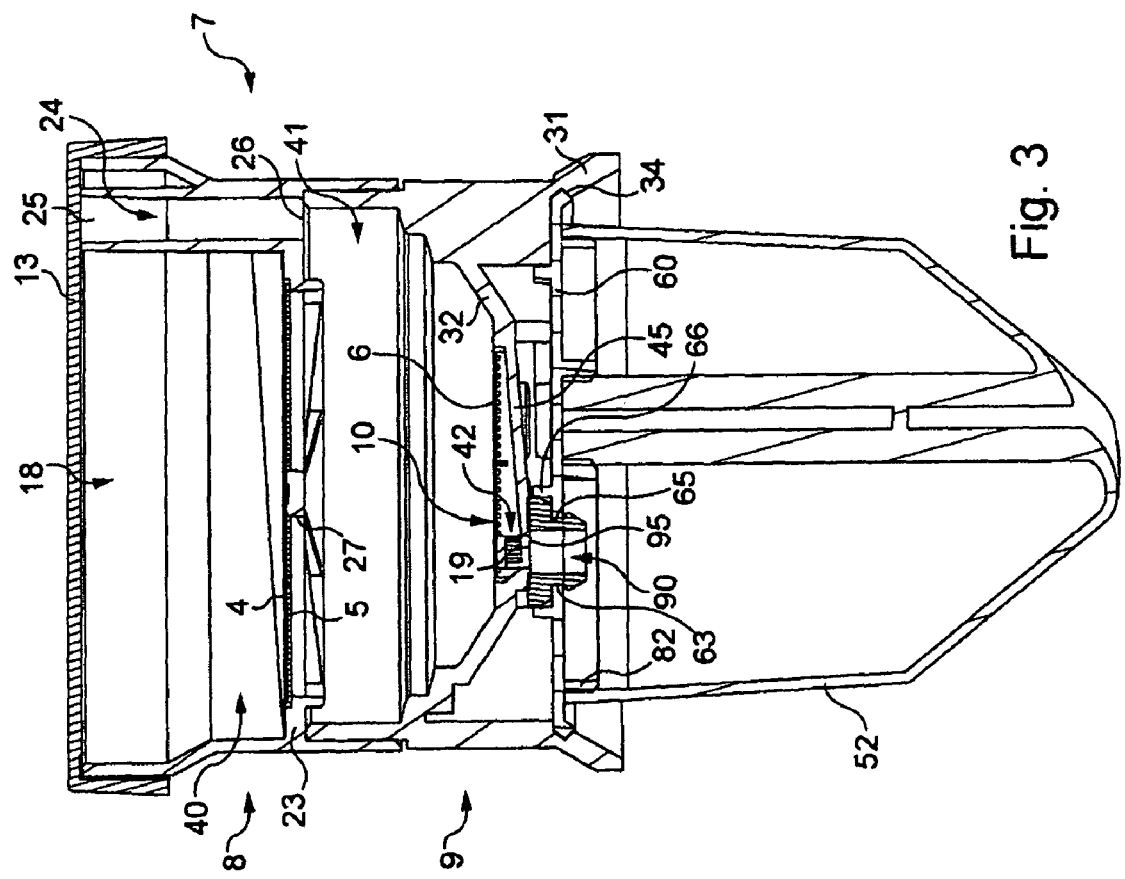
Figure 2:
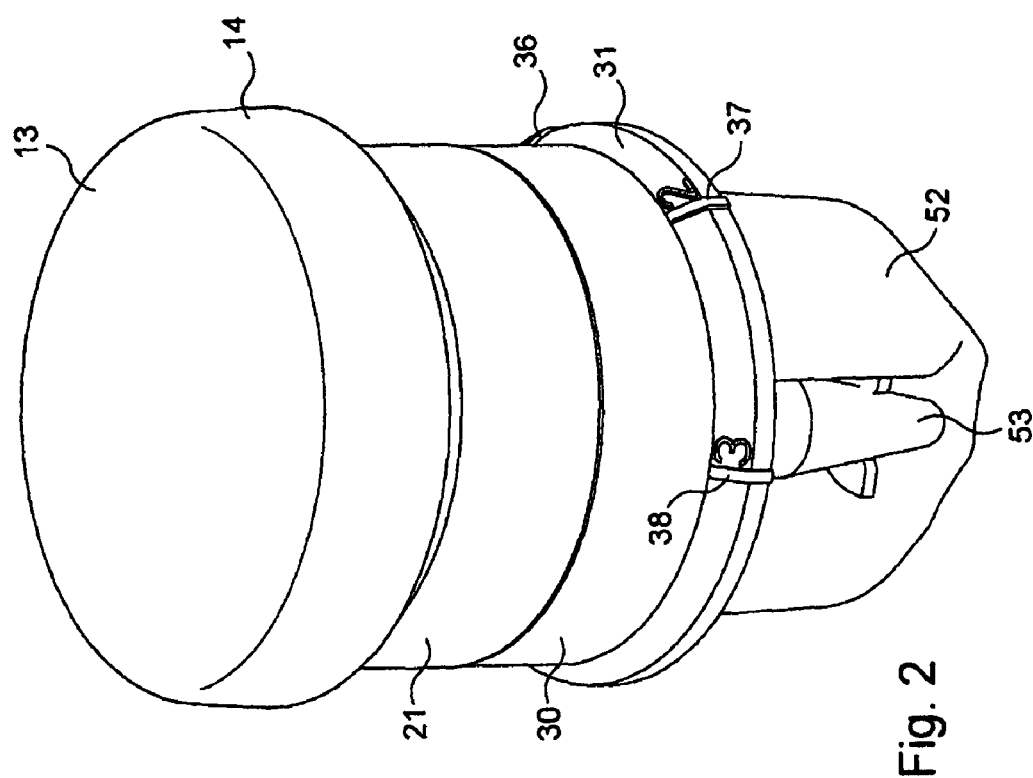
Figure 7:
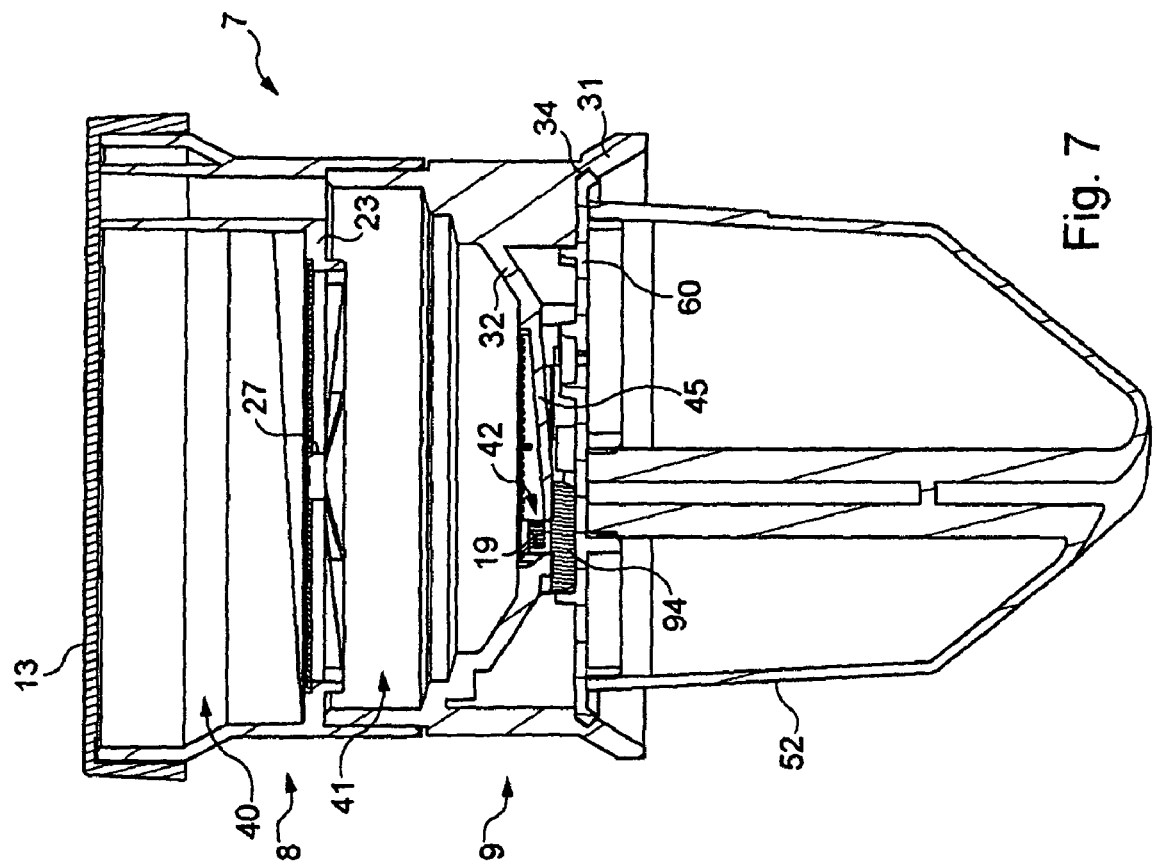

Thus in the position illustrated in FIGS. 2 to 5, the fin 35 is engaged in the cut-out 74 and the collection module is disposed relative to the filter module such that the evacuation opening 19 is situated in register with the opening 95 of the duct 90 of the seal (FIG. 3). The evacuation compartment 42 is thus placed in communication with the reservoir 52 via the duct 90. In this way, the liquid poured into the filter module is able to pass through that module to attain reservoir 52 via the membranes 4 and 5, by the membrane 6 next, and then by passing through the opening 19, the opening 95 and lastly the duct 90.

In this first position, the access to the duct 91 and to the reservoir 53 is obturated by the wall 32 of the lower portion 9 of the filter module, so protecting that reservoir from possible contamination (FIG. 4).

In another relative angular position of the filter module relative to the collection module illustrated in FIGS. 6 to 9, the fin 35 is in the cut-out 80 and the openings 95 and 96 of the ducts 90 and 91 of the seal are obturated by that wall 32. The annular ribs 43 and 44 thus respectively surround the openings 95 and 96 (FIGS. 8 and 9) of the ducts while exerting a pressure against the seal 51 to ensure the fluid-tight isolation of the reservoirs 52 and 53, this being in order to avoid any risk of contamination by the air which would be liable to pass from one reservoir to the other (by evaporation and/or condensation for example).

The opening 19 of that wall is also obturated in fluid-tight manner by the portion 94 of the seal that is situated between the ducts 90 and 91 (FIG. 7), so preventing the liquid from flowing from the filter module.

Figure 11:
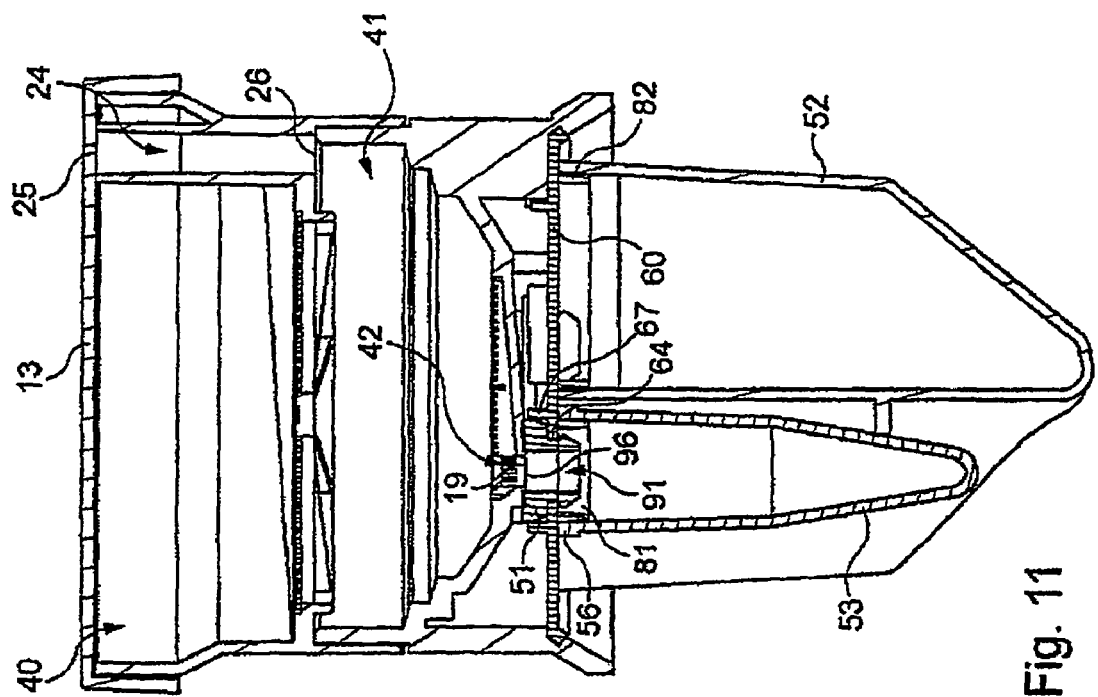

Lastly, in still another relative angular position of the filter module relative to the collection module illustrated in FIGS. 10 to 13, the fin 35 is in the cut-out 77 and the opening 19 is situated in register with the opening 96 of the duct 91 (FIG. 11). In this position the evacuation compartment 42 is placed in communication with the reservoir 53 via the duct 91 whereas the access to the duct 90 of the seal is obturated for it by the wall 32, so protecting the reservoir 52 from possible contamination (FIG. 13). In this way, the liquid coming from the filter module 2 is able to reach the reservoir 53 by passing through the opening 19, the opening 96 and lastly the opening 91 of the seal.

To pass from one position to the other, the operator grasps the preparation unit 1 to rotate the filter module 2 relative to the collection module 3 in order to disengage the fin 35 from the cut-out in which it is disposed. The portions 72, 75, 78 and 79 of the ribs 69, 71 and 70 participate in guiding the fin to enter the corresponding cut-out while the portions 73 and 76 form abutments for that fin in order to prevent the operator from turning the modules relative to each other beyond the authorized angular positions.

A description will now be made of the different steps of preparing a sample to analyze from a liquid to filter which may contain, in the chosen example, not only eukaryote cells but also bacteria whose presence it is desired to detect among those cells.

In order to detect those bacteria they should be separated from the cells contained in the liquid by way of the double stage of filtering presented by the module 2.

In a first step, the operator grasps a preparation unit, and, if it is not already the case, turns the filter module 2 relative to the collection module 3 to position the rib 36 associated with the position "1" on the frusto-conical portion 31 in alignment with the cursor 55 situated on the reservoir 52.

After having removed the cover 11 in advance, the operator then pours a predetermined volume of liquid to analyze into the compartment 40 of the filter module 2 (for example 20 ml).

The operator replaces the cover 11 and the preparation unit 1 is then placed in a centrifuge.

Rotating the centrifuge drives the movement of the liquid such that the predetermined volume passes through the membranes 4 and 5 to occupy the compartment 41 of the filter module.

The large size of the pores of the membranes 4 and 5 means that when those membranes are wet they allow the air to pass only with a slight pressurization (very slight bubble point phenomenon), such that the air can enter the compartment 41 so enabling the liquid then to pass through the membrane 6 and to flow so as to occupy the compartment 42 and lastly, by passing through the aperture 19 and the duct 90, to reach the collection reservoir 52 for the liquid so filtered.

The pore diameter of the membrane 5 (here 5 µm) is chosen such that only the microorganisms of greatest size, here the eukaryotes, are retained by that membrane whereas the other microorganisms, here bacteria (of size well below 5 µm), pass through it to be collected finally on the membrane 6.

The membrane 4, which has pores (here 30 µm) of even greater diameter than those of the membrane 5, is disposed upstream and juxtaposed against the membrane 5 to avoid any risk of clogging of the membrane 5 in case the membrane to filter were to contain a very high number of eukaryote cells to separate from the rest of the liquid.

It is to be noted in this connection that the combination 30 µm/5 µm for the membranes 4 and 5 has real pre-filtration advantages in the separation of mammalian cells from germs since it not only enables relatively large volumes to be entirely filtered (up to 100 ml) and which may be heavily laden with cells to isolate (up to $2.10^8$ cells) but also enables the very great majority of those cells to be retained (approximately 99.9%) while allowing a large quantity of the germs present in the sample to pass (approximately 50%).

Such good results are obtained for pore diameters of the membrane 4 greater than 10 µm and less than 40 µm.

The very small quantity of cells arriving on the filter membrane 6 ($10^5$ cells) thus makes it possible to significantly increase the sensitivity of such a device while reducing the background noise for the nucleic acid amplification techniques (of PRC/TMA type) in order to detect the presence of germs initially present in the filtered liquid with the greatest precision.

The pores of the membrane 6 are of course dimensioned (0.45 µm in this example) so as to retain the germs which it is desired to detect.

During the filling of the reservoir 52, the reduction in the volume of air in that reservoir does not lead to any pressurization phenomenon in that reservoir due to the presence of the opening 65 forming a vent enabling the reservoir 52 and thus the compartment 42 to be kept at atmospheric pressure, which thus prevents any risk of the membrane 6 doming during the filtration of the liquid.

Similarly, the vent 12 (FIG. 1) formed in the cover 11 ensures the compartments 40 and 41 are kept at atmospheric pressure and thus also prevents the membrane 6 doming, not by pressurization in the compartment 42 but by depressurization in the compartments 40 and 41.

Figure 6:
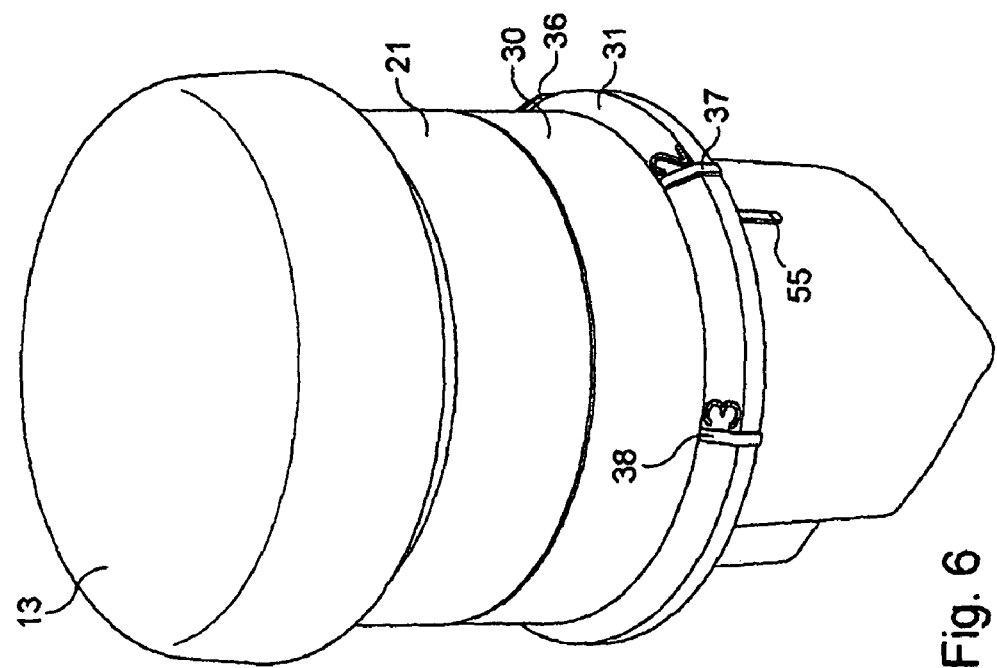

Once this operation has been accomplished, the operator stops the centrifuge and grasps the preparation unit to perform a movement of relative rotation of the filter module relative to the collection module so as to position the rib 37 situated beside the FIG. "2" on the frusto-conical part 31 of the filter module in alignment with the cursor 55 (FIG. 6).

In this position 2, the ducts 90 and 91 are obturated by the transverse wall 32 and the opening 19 is obturated by the solid portion 94 of the seal. In this manner, no flow either of liquid or of air is possible between the compartment 42 of the filter module and the reservoirs 52 and 53.

There is thus no risk of contamination of the reservoir 53 by the liquid contained in the reservoir 52 (by evaporation/condensation).

The operator can then remote the cover 11 to pour into the channel 25 a predetermined volume of a lysing agent (300 µL for example) which, in flowing through that channel, will reach compartment 41 to cover the upper surface 10 of the membrane 6. After having deposited the lysing agent, the operator then replaces the cover 11.

As the vent 65 of the disc 50 and the vent 12 of the cover 11 have enabled the compartments 40, 41 and 42 to be kept at atmospheric pressure, the membrane 6 remains flat which enables the lysing agent to be deposited homogenously and evenly over the whole of the membrane (and not solely at its perimeter which would be the case if the membrane had become domed).

As no liquid flow is possible towards the reservoirs of the collection module, the lysing agent is deliberately kept in contact with the membrane for a predetermined time in order for the lysis of the germs to be as effective as possible.

Figure 10:
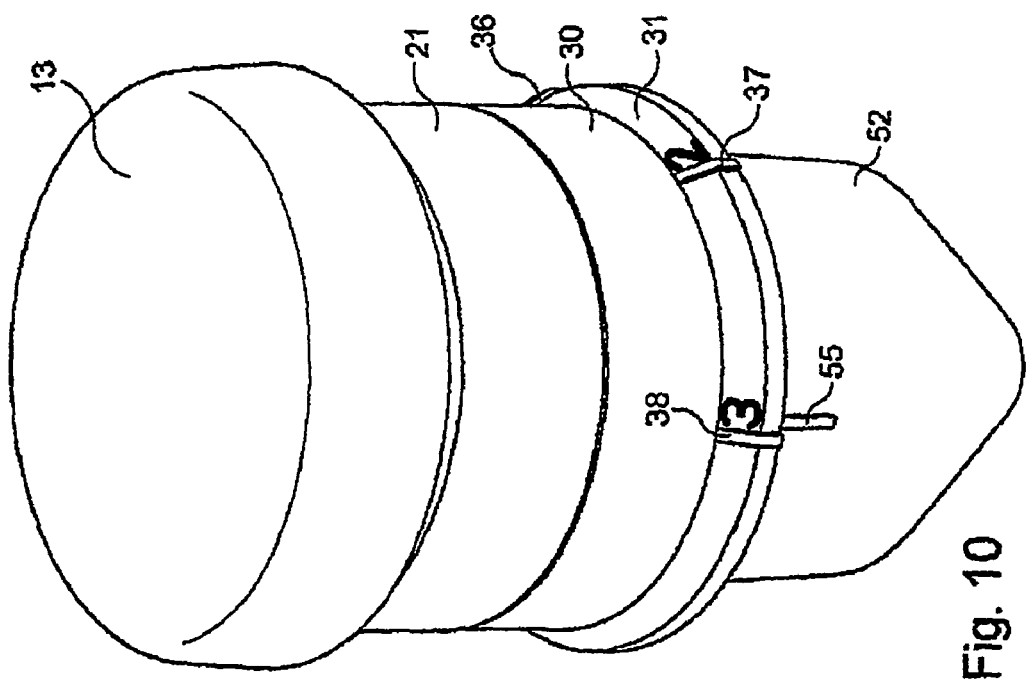

After having kept the lysing agent in contact with the membrane for that predetermined time (depending on the lysing agent) at a predetermined temperature (for example 60°) in order to increase the effectiveness of the agent, the operator again turns the filter module relative to the collection module to position the rib 38 situated beside the FIG. "3" on the frusto-conical part 31 of the filter module in alignment with the cursor 55 (FIG. 10).

The preparation unit is then again placed in the centrifuge to make the lysate (containing the biological material of the bacteria) pass through the equipment 6, that biological material, after having undergone the lysis, being of sufficiently reduced size to pass through the pores of that membrane and thus to be collected in the reservoir 53.

The operator can then remove the preparation unit from the centrifuge and unlatch the reservoir 53 from the disc 50 to perform an analysis of the lysate collected in that reservoir.

It will be noted that the microorganisms to detect are not necessarily bacteria but may in particular be viruses, yeasts (of sufficiently small size not to be retained by the membranes 4 and 5) or moulds. It may be that the liquid to analyze does not contain eukaryote cells but other types of microorganisms (to separate from the germs to detect) such as yeast or filamentous fungi.

Another embodiment of the preparation unit is represented in FIG. 19.

Generally, the same reference numbers are used for similar elements, but increased by 100 for each embodiment.

The preparation unit 101 of FIG. 19 is similar to the unit 1 apart from the reservoir 53 being eliminated in this embodiment, the terminal formation 181 of the disc 150 being in this case provided to be connected for example to a hose 157, as illustrated in FIG. 19, leading to a remote reservoir for example.

In still another embodiment not illustrated, the reservoir 152 is similarly replaced.

Another embodiment of the preparation unit is represented in FIG. 20.

The preparation unit 201 of FIG. 20 comprises a filter module 202 and a collection module 203, the filter module being provided with a membrane 206 with the modules 202 and 203 being rotatably mounted relative to each other.

Like the units 1 and 101, these modules are adapted to have three different relative positions that are identical to those described previously as well as a fourth relative angular position illustrated in FIG. 20 in which the opening 296 of the seal is placed in register with an additional opening 298 formed in a wall of the collection module 203. This opening is obturated by a heat-sealed film (not illustrated) that the operator can detach such that the reservoir 253 is made accessible in order to be able to directly take off therefrom the liquid it contains using a pipette 99 rather than unlatching that reservoir 253 from the rest of the collection module 203.

In another embodiment, not illustrated, the cover 11 is replaced, in particular when it is impossible to work under an extractor hood or in a confined space protected from contaminations, by a cover provided to be welded to the body of the filter module in order to reduce the risk of contamination, that cover then having, in that case, a first terminal formation (of female Luer type for example) to connect a valve by which the volume of liquid to filter is introduced, a second terminal formation, also of female Luer type, to connect a microbiological filter comprising a membrane that forms a barrier to microorganisms (porosity 0.22 μm) but permeable to the air in order therefore to enable sterile venting of the compartment 40, as well as a third female Luer terminal formation to connect a syringe provided with a male Luer terminal formation, that third terminal formation issuing in the access channel 24 and being obturated by a plug when the syringe is not connected to that terminal formation.

In another embodiment, not illustrated, the preparation unit lacks the membranes 4 and 5 and only comprises the filter membrane 6 and/or that membrane 6 is not of PVDF but of polyestersulfone (PES) for example.

It is also to be noted that the preparation unit according to the invention may also be used for any other filtration method instead of the one described above for example for a filtration method in which the lysis is not carried out by a liquid chemical agent but by emitting ultrasound towards the membrane 6 or by micro-wave heating of that membrane and then by retrieving the biological material that underwent the lysis on the membrane by passing a collection liquid into the preparation unit which is collected in the reservoir 53.

More generally, the preparation unit may also be used for any other filtration method requiring liquids to be collected in at least two different receptacles.

The present invention is not limited to the embodiments described and represented but encompasses any variant form thereof.

The invention claimed is:

1. A unit for preparing a sample for the microbiological analysis of a predetermined volume of liquid that may contain microorganisms, said unit comprising a filter module and a collection module for receiving liquid coming from said filter module, with said filter module comprising an inlet compartment for inletting said predetermined volume by an inlet opening of said filter module, said inlet compartment being adapted to contain the whole of said predetermined volume, as well as an evacuation compartment for evacuating said predetermined volume by an evacuation opening of said filter module to said collection module, said evacuation compartment being separated from said inlet compartment by a filter membrane, the filter and collection modules being rotatably mounted relative to each other, and having, relative to each other, a first relative predetermined position, in which said evacuation opening of said filter module is in register with a first opening of said collection module and a second relative predetermined position different from said first position, in which said evacuation opening of said filter module is in register with a second opening of said collection module characterized in that said inlet and evacuation compartments are on opposite sides from each other relative to said filter membrane with said inlet compartment being arranged such that, when said predetermined volume is in said inlet compartment the liquid is in contact with the filter membrane over at least the majority of its surface; wherein said filter module comprises a body within which is fixed said filter membrane as well as a separation membrane that is situated between said inlet opening and said filter membrane, said separation membrane having a pore diameter greater than the pore diameter of said filter membrane, and wherein said filter module comprises another opening formed in said body and giving access to a compartment of said body situated between said separation and filter membranes.

2. A unit according to claim 1, wherein in said first predetermined position, said second opening is obturated and in that, in said second predetermined position, said first opening is obturated.

3. A unit according to claim 1, wherein said filter and collection modules also have another predetermined position relative to each other, termed obturating position, different from the first and second positions, in which said evacuation opening is obturated.

4. A unit according to claim 3, wherein in said obturating position, said first and second openings are also obturated.

5. A unit according to claim 1, wherein said filter and collection modules also have another predetermined position relative to each other, termed take-off position, different from the first and second positions, in which said second opening is in register with a take-off opening that said unit comprises.

6. A unit according to claim 1, wherein said separation membrane is fixed to a first portion of said body and said filter membrane is fixed to a second portion of said body, with said first and second portions being adapted to be nested one inside the other and welded together.

7. A unit according to claim 1, wherein said filter module comprises another membrane juxtaposed against said separation membrane, on the opposite side of the separation membrane to the filter membrane, said another membrane having a greater pore diameter than the pore diameter of said separation membrane.

8. A unit according to claim 1, wherein the pore diameter of said separation membrane is greater than 1 μm.

9. A unit according to claim 1, wherein the pore diameter of said filter membrane is less than 1 μm.

10. A unit according to claim 1, wherein said another opening is situated at the end of a channel formed in said body.

11. A unit according to claim 10, wherein said another opening is substantially situated at the same level as the inlet opening that may contain microorganisms.

12. A unit according to claim 1, wherein said collection module comprises a disc of which the perimeter is adapted to be received in an annular groove that said filter module comprises.

13. A unit according to claim 1, wherein said filter module comprises indexing means and said collection module comprises complementary indexing means for each predetermined position of the filter module relative to the collection module.

14. A unit according to claim 13, wherein said indexing means comprises a fin and in that said complementary indexing means comprises ribs, each rib having a cut-out adapted to receive said fin.

15. A unit according to claim 1, wherein said first opening of the collection module issues to a reservoir that said collection module comprises.

16. A unit according to claim 15, wherein the collection module comprises a vent adapted allow air to pass into said reservoir.

17. A unit according to claim 15, wherein said reservoir has a crescent-shaped cross-section.

18. A unit according to claim 1, wherein said second opening of the collection module issues to a reservoir that said collection module comprises and said reservoir has latching means adapted to cooperate with complementary latching means that said collection module comprises.

19. A unit according to claim 1, wherein said collection module comprises a seal in which are formed two ducts, each respectively issuing, on the same side as the filter module, by said first opening and by said second opening.

20. A unit according to claim 19, wherein said seal has a bean-shaped cross-section.

21. A unit according to claim 1, wherein said filter module comprises a vent adapted to allow air to pass into said inlet compartment.

22. A unit for preparing a sample for the microbiological analysis of a predetermined volume of liquid that may contain microorganisms, said unit comprising a filter module and a collection module for receiving liquid coming from said filter module, with said filter module comprising an inlet compartment for inletting said predetermined volume by an inlet opening of said filter module, said inlet compartment being adapted to contain the whole of said predetermined volume, as well as an evacuation compartment for evacuating said predetermined volume by an evacuation opening of said filter module to said collection module, said evacuation compartment being separated from said inlet compartment by a filter membrane, the filter and collection modules being rotatably mounted relative to each other, and having, relative to each other, a first relative predetermined position, in which said evacuation opening of said filter module is in register with a first opening of said collection module and a second relative predetermined position different from said first position, in which said evacuation opening of said filter module is in register with a second opening of said collection module characterized in that said inlet and evacuation compartments are on opposite sides from each other relative to said filter membrane with said inlet compartment being arranged such that, when said predetermined volume is in said inlet compartment the liquid is in contact with the filter membrane over at least the majority of its surface, wherein said second opening of the collection module issues to a reservoir that said collection module comprises, and wherein said reservoir has latching means adapted to cooperate with complementary latching means that said collection module comprises.

* * * * *